(12) United States Patent
Niddam-Hildesheim et al.

(10) Patent No.: US 8,063,250 B2
(45) Date of Patent: Nov. 22, 2011

(54) CRYSTAL FORMS OF O-DESMETHYLVENLAFAXINE FUMARATE

(75) Inventors: Valerie Niddam-Hildesheim, Kadima (IL); Eli Lancry, Modiin (IL); Sharona Shachan-tov, Kfar-Saba (IL); Sigalit Levi, Modi'in (IL); Tamar Nidam, Yehud (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 414 days.

(21) Appl. No.: 12/313,961

(22) Filed: Nov. 26, 2008

(65) Prior Publication Data

US 2009/0170948 A1 Jul. 2, 2009

Related U.S. Application Data

(60) Provisional application No. 61/004,359, filed on Nov. 26, 2007, provisional application No. 61/090,282, filed on Aug. 20, 2008, provisional application No. 61/095,398, filed on Sep. 9, 2008, provisional application No. 61/095,712, filed on Sep. 10, 2008.

(51) Int. Cl.
C07C 213/00 (2006.01)
(52) U.S. Cl. ........ 564/360; 564/336; 514/557; 562/512; 562/590; 562/597
(58) Field of Classification Search .................. None
See application file for complete search history.

(56) References Cited

U.S. PATENT DOCUMENTS

| | | | |
|---|---|---|---|
| 4,535,186 A * | 8/1985 | Husbands et al. ............ 564/336 |
| 6,197,828 B1 | 3/2001 | Jerussi et al. | |
| 6,673,838 B2 | 1/2004 | Hadfield et al. | |
| 6,689,912 B2 | 2/2004 | Weber | |
| 7,026,508 B2 | 4/2006 | Winkley et al. | |
| 2002/0022662 A1 * | 2/2002 | Yardley et al. ................ 514/649 |
| 2003/0045583 A1 | 3/2003 | Hadfield et al. | |
| 2004/0106818 A1 | 6/2004 | Zhiyin et al. | |
| 2005/0096479 A1 | 5/2005 | Hadfield et al. | |
| 2005/0197392 A1 | 9/2005 | Jerussi et al. | |
| 2006/0047125 A1 | 3/2006 | Leonardi et al. | |
| 2007/0135449 A1 | 6/2007 | Mahaney et al. | |

FOREIGN PATENT DOCUMENTS

| | | |
|---|---|---|
| CN | 1240206 | 1/2000 |
| EP | 0 112 669 A2 | 7/1984 |
| GB | 2 173 787 A | 10/1986 |
| WO | WO 9620160 | 7/1996 |
| WO | WO 00/59851 A1 | 10/2000 |
| WO | WO 02/18325 | 3/2002 |
| WO | WO 02/50017 | 6/2002 |
| WO | WO 02/064543 A2 | 8/2002 |
| WO | WO 2007/011594 A2 | 1/2007 |
| WO | WO 2007/120923 A1 | 10/2007 |
| WO | WO 2008/015584 A2 | 2/2008 |
| WO | WO 2008/017886 | 2/2008 |
| WO | WO 2008/047167 | 4/2008 |

OTHER PUBLICATIONS

Yardley, John P., et al., 2-Phenyl-2-(1-hydroxycycloalkyl)ethylamine Derivatives: Synthesis and Antidepressant Activity, J. Med. Chem. (1990) 33, pp. 2899-2905, XP000891765.

Klamerus, K.J. et al., "Introduction of the Composite Parameter to the Pharmokinetics of Venlafaxine and its Active O-Desmethyl Metabolite," J. Clin. Pharmacol. (1992) vol. 32(8), pp. 716-724.

Database Beilstein, Beilstein Institute for Organic Chemistry, retrieved from XFIRE, XP002466133; Database accession No. BRN 4915303 abstract & Bull. Soc. Chim. Fr (1967) pp. 2110-2116.

International Search Report of PCT/US2008/013170 dated Sep. 29, 2009.

G.P.R. Carr, "The Development of British Pharmacopoeia Monographs for Idoxuridine and Idoxuridine Eye Drops Using High-Pressure Liquid Chromatography for Essay and for Controlling Related Impurities", Journal of Chromatography, 157 (1978), pp. 171-184.

Hicks, David. R. et al., "A High-Performance Liquid Chromatographic Methods for the Simultaneous Determination of Venlafaxine and O-Desmethylvenlafaxine in Biological Fluids", Therapeutic Drug Monitoring, vol. 16, (1994), pp. 100-107.

Kumar, Phani. A. et al., "A Validated Reversed Phase HPLC Method for the Determination of Process-Related Impurities in Almotriptan Malate API", Journal of Pharmaceutical and Biomedical Analysis, vol. 46, No. 4, (2007),pp. 792-798.

Rao, Nageswara. R. et al., "An Overview of the Recent Trends in Development of HPLC Methods for Determination of Impurities in Drugs", Journal of Pharmaceutical and Biomedical Analysis, vol. 33, No. 3, (2003), pp. 335-377.

* cited by examiner

*Primary Examiner* — Sudhakar Katakam
(74) *Attorney, Agent, or Firm* — Kenyon & Kenyon LLP

(57) ABSTRACT

Provided are crystalline forms of O-desmethylvenlafaxine fumarate, methods for their preparation, and pharmaceutical compositions thereof.

40 Claims, 6 Drawing Sheets a solid-state $^{13}$C NMR spectrum of ODV Fumarate Form I in the 110-200 ppm range.

CRYSTAL FORMS OF O-DESMETHYLVENLAFAXINE FUMARATE

CROSS REFERENCE TO RELATED APPLICATIONS

The present invention claims the benefit of the following U.S. Provisional Patent Application Nos. 61/004,359, filed Nov. 26, 2007; 61/090,282, filed Aug. 20, 2008; 61/095,398, filed Sep. 9, 2008; and 61/095,712, filed Sep. 10, 2008. The contents of these applications are incorporated herein by reference.

FIELD OF THE INVENTION

The present invention is directed to crystalline forms of O-desmethylvenlafaxine fumarate and methods of preparation thereof.

BACKGROUND OF THE INVENTION

Venlafaxine, (±)-1-[2-(Dimethylamino)-1-(4-methyoxyphenyl)ethyl]cyclo-hexanol, having the following formula I, is the first of a class of anti-depressants. Venlafaxine acts by inhibiting re-uptake of norepinephrine and serotonin, and is an alternative to the tricyclic anti-depressants and selective re-uptake inhibitors.

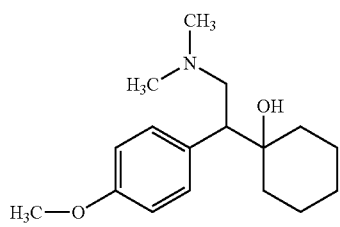

formula I

O-desmethylvenlafaxine, chemically named 4-[2-(dimethylamino)-1-(1-hydroxycyclohexyl)ethyl]phenol and having the following formula II

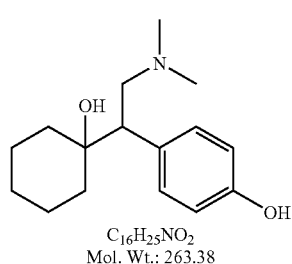

formula II $C_{16}H_{25}NO_2$
Mol. Wt.: 263.38 is a major metabolite of venlafaxine and has been shown to inhibit norepinephrine and serotonin uptake. Klamerus, K. J. et al., "Introduction of the Composite Parameter to the Pharmacokinetics of Venlafaxine and its Active O-Desmethyl Metabolite", J. Clin. Phavmacol. 32:716-724 (1992).

O-desmethylvenlafaxine and processes for the preparation thereof are described in U.S. Pat. Nos. 6,197,828 and 6,689,912, and in US 2005/0197392, which are incorporated herein by reference.

The fumarate salt of O-desmethylvenlafaxine, is chemically named -[2-(dimethylamino)-1-(4-phenol) ethyl]-cyclohexanol fumarate, and has the following formula III

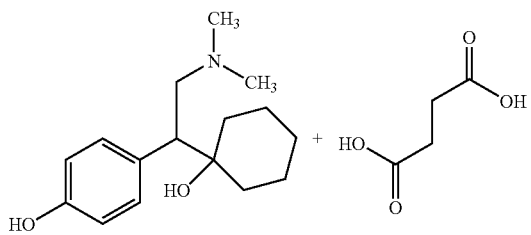

Formula III

Several pharmaceutically acceptable salts of O-desmethylvenlafaxine are described in U.S. Pat. No. 4,535,186. In Example 26 of this reference, a preparation of the fumarate salt is described. The product is reported to have a melting point range of 140° C.-142° C.

Polymorphism, the occurrence of different crystal forms, is a property of some molecules and molecular complexes. A single molecule or molecular complex, like O-desmethylvenlafaxine fumarate, may give rise to a variety of crystalline forms having distinct crystal structures and physical properties like melting point, x-ray diffraction pattern (e.g. powder x-ray diffraction or PXRD), infrared absorption fingerprint, FTIR spectrum, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubilities.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

There is a need in the art for polymorphic forms of O-desmethylvenlafaxine fumarate.

SUMMARY OF THE INVENTION

In one embodiment, the present invention provides a crystalline form of O-desmethylvenlafaxine fumarate, characterized by data selected from the group consisting of: a powder XRD pattern having any 5 peaks selected from the group consisting of peaks at about: 5.3, 10.5, 12.1, 15.5, 17.9, 21.0, 22.1, 22.7, 23.8 and 24.2 degrees two theta±0.2 degrees two theta, wherein the combination of peaks selected includes at least one of the peaks at about 12.1, 17.9, 22.1 or 23.8±0.2 degrees two theta±0.2 degrees two theta; a PXRD pattern having reflections at about: 5.3, 10.5, 12.1, 15.5 and 17.9 degrees two theta±0.2 degrees two theta; a powder XRD pattern having peaks at about 5.3, 10.5, 12.1 degrees two theta±0.2 degrees two theta and at least two peaks selected from the following list of peaks at about: 15.5, 16.9, 19.0, 21.0, 24.2, 25.3, and 26.4±0.2 degrees two theta±0.2 degrees two theta; a powder XRD pattern substantially as depicted in FIG. 1; a solid-state $^{13}$C NMR spectrum with signals at about 114.89, 139.68 and 172.44±0.2 ppm; a solid-state $^{13}$C NMR spectrum having chemical shifts differences between the signal exhibiting the lowest chemical shift and another in the chemical shift range of 110 to 200 ppm of about 0, 24.79 and 57.55±0.1 ppm, wherein the signal exhibiting the lowest chemical shift in the chemical shift area of 110 to 200 ppm is at about 114.89±1 ppm; a solid state $^{13}$C NMR spectrum substantially as depicted in FIG. 4; a solid state $^{13}$C NMR spectrum substantially as depicted in FIG. 5; and combinations thereof.

In another embodiment, the present invention provides a crystalline form of O-desmethylvenlafaxine fumarate, characterized by data selected from the group consisting of: a powder XRD pattern having any 5 peaks selected from the group consisting of peaks at about: 5.3, 10.5, 11.6, 16.4, 18.4, 21.0, 23.4, 24.3, 26.4 and 31.4 degrees two theta±0.2 degrees two theta, wherein the combination of peaks selected includes at least one of the peaks at about 11.6, 23.4 or 31.4±0.2 degrees two theta±0.2 degrees two theta; a PXRD pattern having reflections at about: 5.3, 10.5, 11.6, 16.4 and 18.4 degrees two theta±0.2 degrees two theta; a powder XRD pattern having peaks at about 14.2, 16.4, 18.4 degrees two theta±0.2 degrees two theta, and at least two peaks selected from the following list of peaks at about: 5.3, 10.5, 11.6, 20.8, 24.3, and 26.4±0.2 degrees two theta±0.2 degrees two theta; a powder XRD pattern substantially as depicted in FIG. 2; a solid-state $^{13}$C NMR spectrum with signals at about 114.59, 126.44 and 133.99±0.2 ppm; a solid-state $^{13}$C NMR spectrum having chemical shifts differences between the signal exhibiting the lowest chemical shift and another in the chemical shift range of 110 to 200 ppm of about 0, 11.85 and 19.4±0.1 pp, wherein the signal exhibiting the lowest chemical shift in the chemical shift area of 110 to 200 ppm is at about 114.59±1 ppm; a solid state $^{13}$C NMR spectrum substantially as depicted in FIG. 6; a solid state $^{13}$C NMR spectrum substantially as depicted in FIG. 7; and combinations thereof.

DETAILED DESCRIPTION OF THE INVENTION

The present invention is directed to crystalline forms of O-desmethylvenlafaxine fumarate, in particular crystalline pure forms of such crystalline O-desmethylvenlafaxine fumarate.

As used herein the term "crystalline pure" or "pure" refers to a crystalline form of O-desmethylvenlafaxine fumarate containing at least 50% by weight of one crystalline form of O-desmethylvenlafaxine. Preferably, at least 60% by weight, at least 80% by weight, at least 90% by weight, at least 95% by weight, or at least 99% by weight. For example, between about 60% and 95% by weight or between about 70% and 90% by weight. Alternatively, "crystalline pure" or "pure" refers to a crystalline form of O-desmethylvenlafaxine fumarate containing less than a certain amount of another crystalline form, for example, less than about 10% by weight, less than about 5% by weight, less than about 1% by weight.

As used herein the term "reduced pressure" refers to a pressure of less than 1 atmosphere, preferably less than 100 mm Hg.

As used herein the term "elevated temperature" refers to a temperature above room temperature. As used herein, the term "room temperature" refers to a temperature of about 15° C. to about 30° C., preferably, about 18° C. to about 25° C.

As used herein the term "volume" refers to ml of solvent per gram of material.

Figure 1:
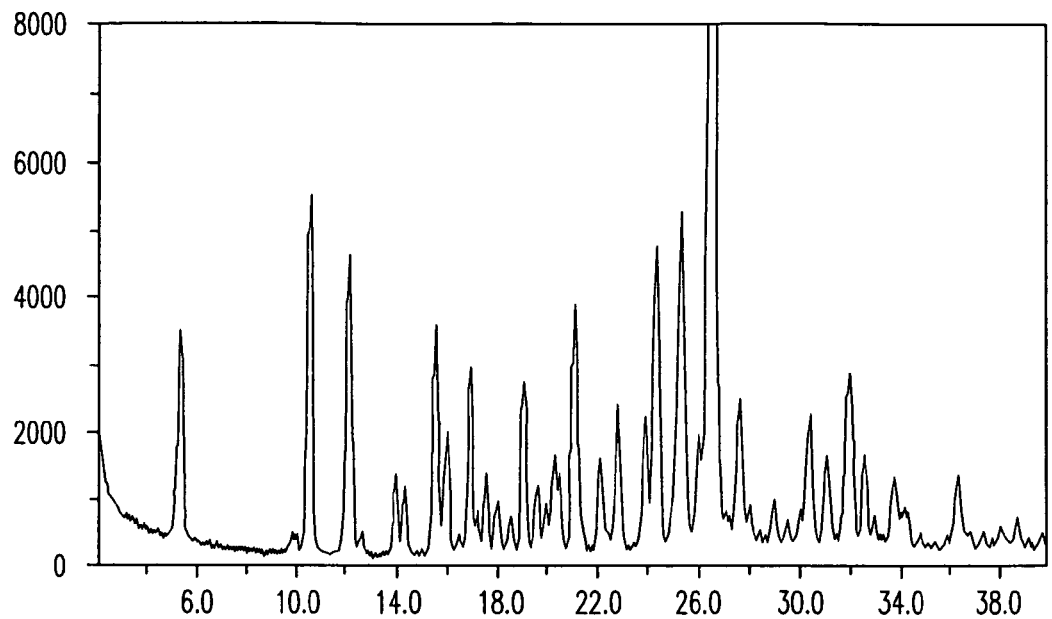
FIG. 1 illustrates a PXRD for crystalline Form I of O-desmethylvenlafaxine fumarate.
Figure 4:
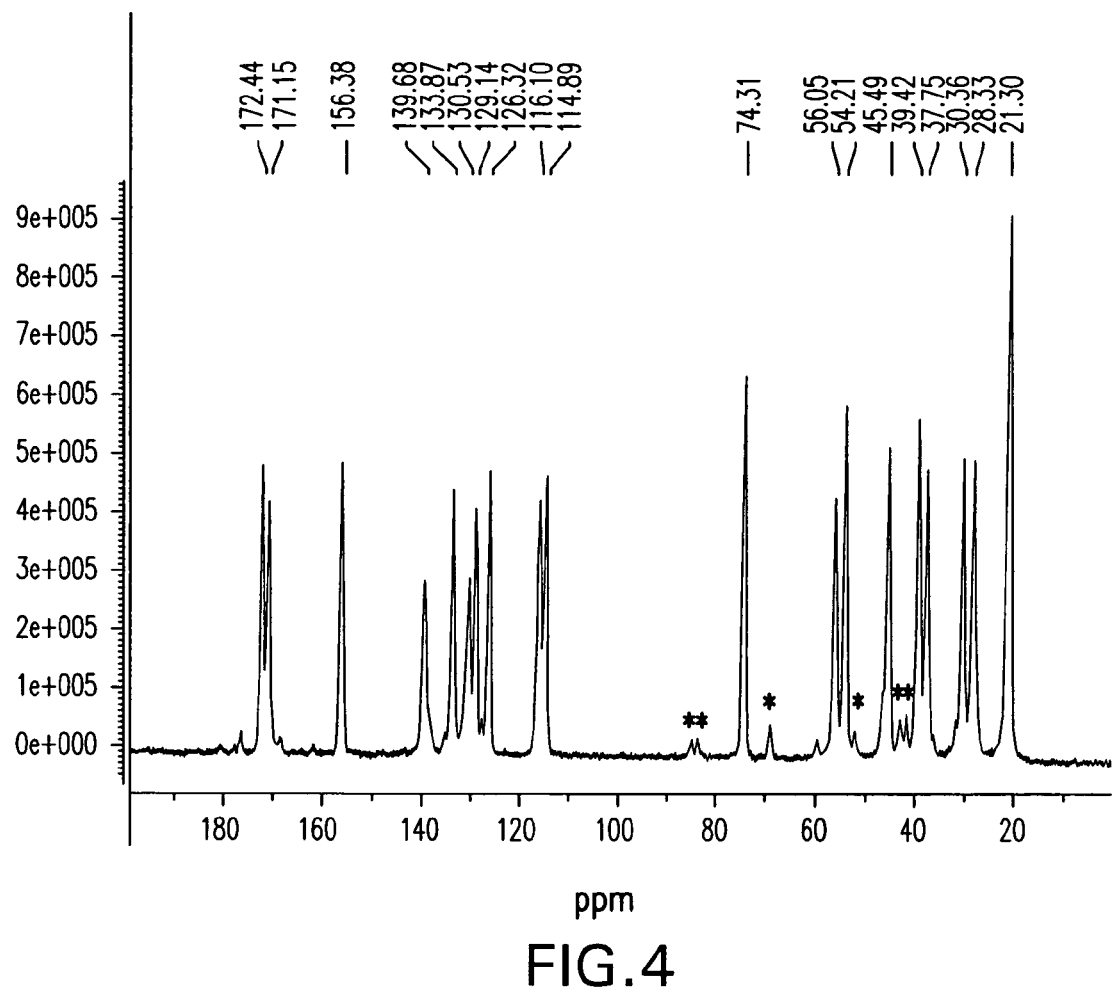
FIG. 4 illustrate a solid-state $^{13}$C NMR spectrum for Form I of O-desmethylvenlafaxine fumarate at the range 0-200 ppm.
Figure 5:
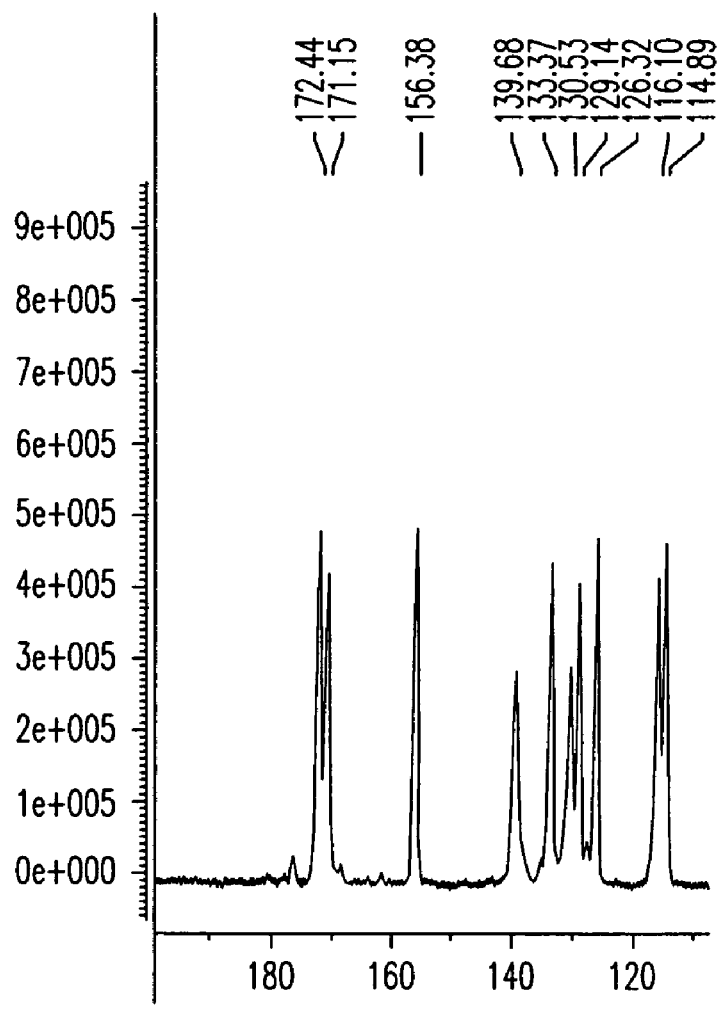
FIG. 5. illustrate a solid-state $^{13}$C NMR spectrum for Form I of O-desmethylvenlafaxine fumarate at the range 110-200 ppm.

In one embodiment, the present invention provides a crystalline form of O-desmethylvenlafaxine fumarate (denominated as Form I), characterized by data selected from the group consisting of: a powder XRD pattern having any 5 peaks selected from the group consisting of peaks at about: 5.3, 10.5, 12.1, 15.5, 17.9, 21.0, 22.1, 22.7, 23.8 and 24.2 degrees two theta±0.2 degrees two theta, wherein the combination of peaks selected includes at least one of the peaks at about 12.1, 17.9, 22.1 or 23.8±0.2 degrees two theta±0.2 degrees two theta; a PXRD pattern having reflections at about: 5.3, 10.5, 12.1, 15.5 and 17.9 degrees two theta±0.2 degrees two theta; a powder XRD pattern having peaks at about 5.3, 10.5, 12.1 degrees two theta±0.2 degrees two theta and at least two peaks selected from the following list of peaks at about: 15.5, 16.9, 19.0, 21.0, 24.2, 25.3, and 26.4±0.2 degrees two theta±0.2 degrees two theta; a powder XRD pattern substantially as depicted in FIG. 1; a solid-state $^{13}$C NMR spectrum with signals at about 114.89, 139.68 and 172.44±0.2 ppm; a solid-state $^{13}$C NMR spectrum having chemical shifts differences between the signal exhibiting the lowest chemical shift and another in the chemical shift range of 110 to 200 ppm of about 0, 24.79 and 57.55±0.1 ppm, wherein the signal exhibiting the lowest chemical shift in the chemical shift area of 110 to 200 ppm is at about 114.89±1 ppm; a solid state $^{13}$C NMR spectrum substantially as depicted in FIG. 4; a solid state $^{13}$C NMR spectrum substantially as depicted in FIG. 5; and combinations thereof.

Figure 2:
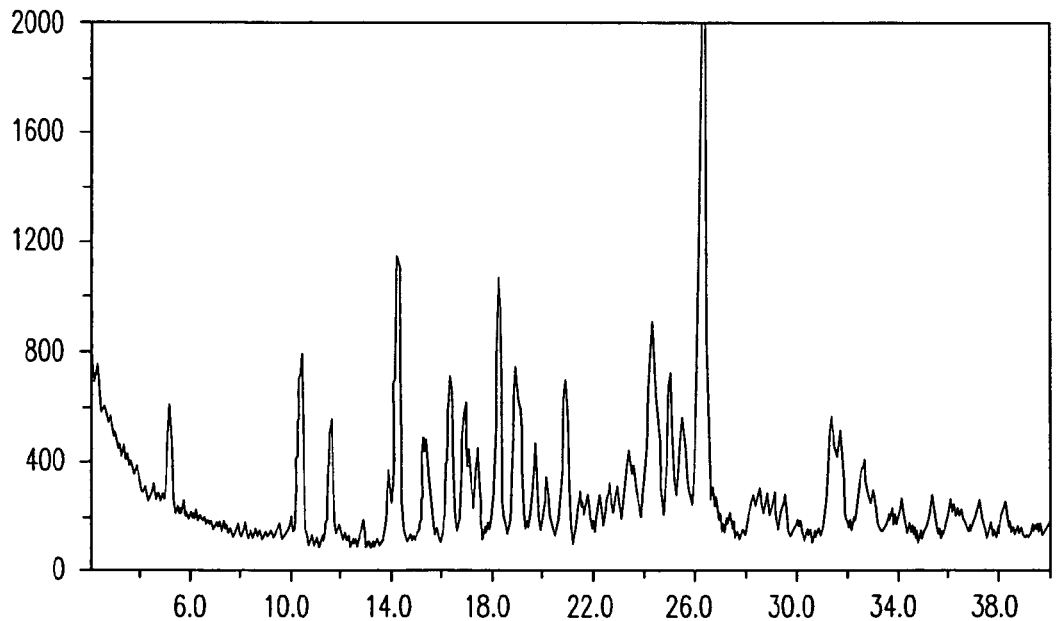
FIG. 2 illustrates a PXRD for crystalline Form II of O-desmethylvenlafaxine fumarate.
Figure 6:
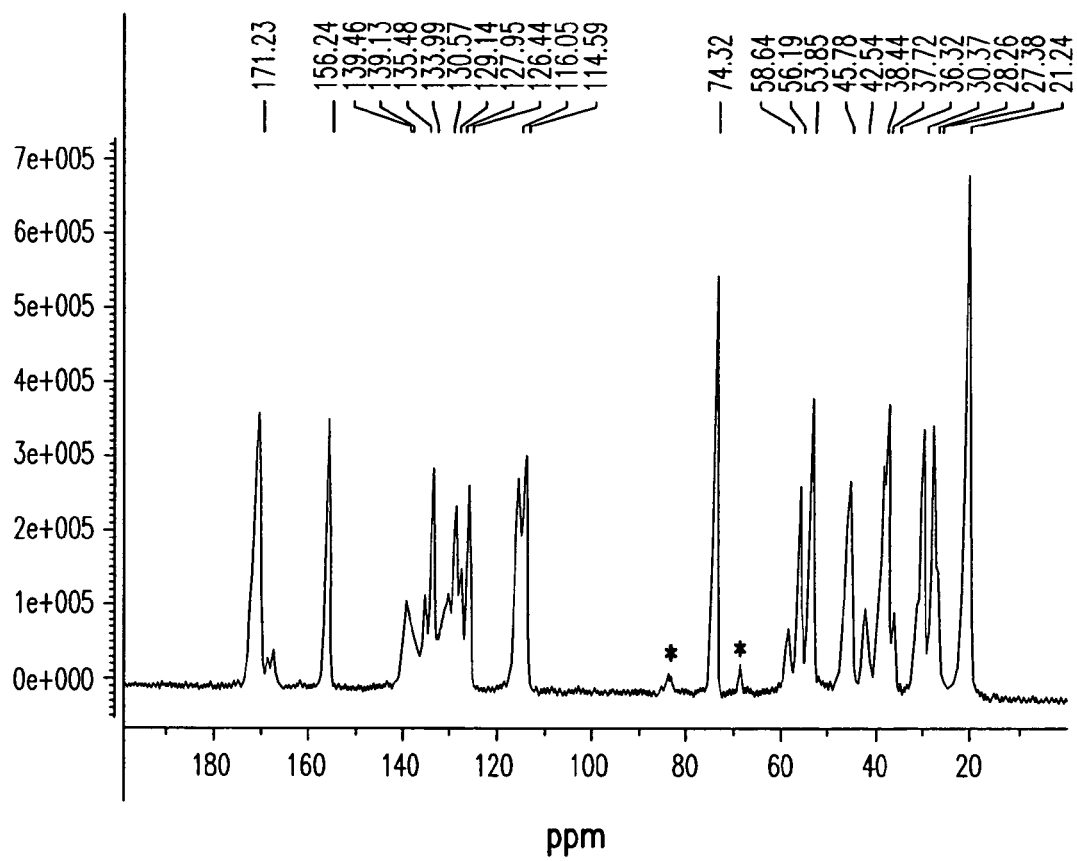
FIG. 6 illustrate a solid-state $^{13}$C NMR spectrum for Form II of O-desmethylvenlafaxine fumarate at the range 0-200 ppm.
Figure 7:
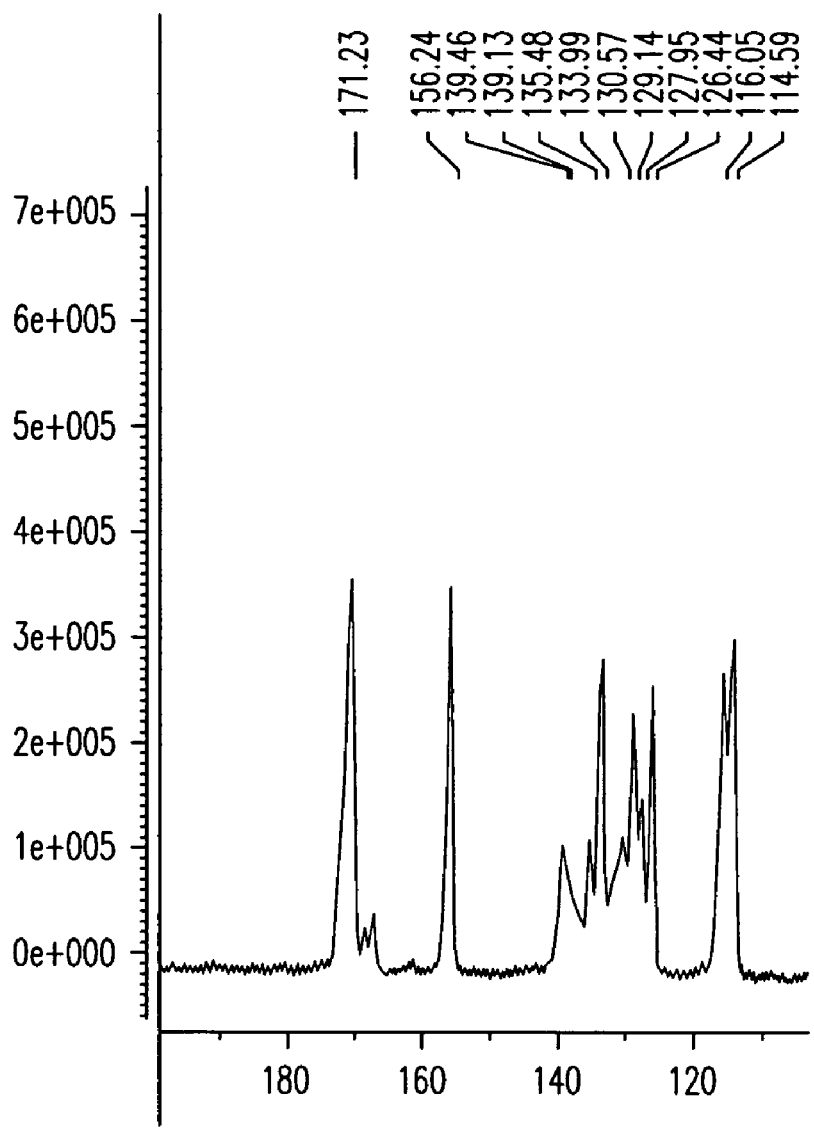
FIG. 7 illustrate a solid-state $^{13}$C NMR spectrum for Form II of O-desmethylvenlafaxine fumarate at the range 110-200 ppm.

In another embodiment, the present invention provides a crystalline form of O-desmethylvenlafaxine fumarate (denominated as Form II), characterized by data selected from the group consisting of: a powder XRD pattern having any 5 peaks selected from the group consisting of: peaks at about 5.3, 10.5, 11.6, 16.4, 18.4, 21.0, 23.4, 24.3, 26.4 and 31.4 degrees two theta±0.2 degrees two theta, wherein the combination of peaks selected includes at least one of the peaks at about 11.6, 23.4 or 31.4±0.2 degrees two theta±0.2 degrees two theta; a PXRD pattern having reflections at about: 5.3, 10.5, 11.6, 16.4 and 18.4 degrees two theta±0.2 degrees two theta; a powder XRD pattern having peaks at about 14.2, 16.4, 18.4, and at least two peaks selected from the following list of peaks at about: 5.3, 10.5, 11.6, 20.8, 24.3, and 26.4±0.2 degrees two theta±0.2 degrees two theta; a powder XRD pattern substantially as depicted in FIG. 2; a solid-state $^{13}$C NMR spectrum with signals at about 114.59, 126.44 and 133.99±0.2 ppm; a solid-state $^{13}$C NMR spectrum having chemical shifts differences between the signal exhibiting the lowest chemical shift and another in the chemical shift range of 110 to 200 ppm of about 0, 11.85 and 19.4±0.1 ppm wherein the signal exhibiting the lowest chemical shift in the chemical shift area of 110 to 200 ppm is at about 114.59±1 ppm; a solid state $^{13}$C NMR spectrum substantially as depicted in FIG. 6; a solid state $^{13}$C NMR spectrum substantially as depicted in FIG. 7; and combinations thereof.

In a preferred embodiment, the present invention describes pure crystalline Form I of O-desmethylvenlafaxine fumarate. Preferably, pure Form I of O-desmethylvenlafaxine fumarate contains less than about 50%, preferably less than about 40%, more preferably less than about 30%, even more preferably less than about 20%, even more preferably less than about 10%, even more preferably less than about 5%, and most preferably less than about 1% by weight of crystalline Form II of O-desmethylvenlafaxine fumarate.

The purity of crystalline Form I of O-desmethylvenlafaxine fumarate can be determined by using solid state analytical methods such as X-ray diffraction (XRD), solid state $^{13}$C NMR (SS-$^{13}$C NMR) or other known methods for determining the purity of crystalline forms. For example, in powder XRD diffractograms, the peaks at 11.6, 23.4 or 31.4±0.2 degrees two theta are attributed to crystalline Form II of O-desmethylvenlafaxine fumarate only and will not appear in the diffractogram for pure crystalline Form I of O-desmethylvenlafaxine fumarate. In the SS-$^{13}$C NMR spectrum of pure crystalline Form I of O-desmethylvenlafaxine fumarate the following signals at 139.46, 139.13, 135.48, 127.95, 58.64, 53.85, 42.54, 38.44, 36.32±0.2 ppm, which are attributed to crystalline Form II of O-desmethylvenlafaxine fumarate will not be detected.

In a preferred embodiment the present invention describes pure crystalline Form II of O-desmethylvenlafaxine fumarate. Preferably, pure crystalline Form II of O-desmethylvenlafaxine fumarate contains less than about 50%, preferably less than about 40%, more preferably less than about 30%, even more preferably less than about 20%, even more preferably less than about 10%, even more preferably less than about 5%, and most preferably less than about 1% by weight of crystalline Form I of O-desmethylvenlafaxine fumarate.

The purity of crystalline O-desmethylvenlafaxine Form II can be determined by using solid state analytical methods such as powder XRD, SS-$^{13}$C NMR or other known methods for determining the purity of crystalline forms. For example, in the XRD diffractograms, the peaks at 12.1, 16.0 or at 25.3±0.2 degrees two theta are attributed to crystalline O-desmethylvenlafaxine fumarate Form I only and will not appear in the diffractogram of pure crystalline O-desmethylvenlafaxine fumarate Form II. In the SS-$^{13}$C NMR spectrum of pure crystalline Form II of O-desmethylvenlafaxine fumarate the following signals at 172.44, 54.21 or 39.42±0.2 ppm which are attributed to crystalline O-desmethylvenlafaxine fumarate Form I will not be detected.

In another embodiment, the present invention provides a process for preparing crystalline O-desmethylvenlafaxine fumarate Form I comprising: providing a mixture of O-desmethylvenlafaxine, a $C_{1-4}$ alcohol solvent, preferably isopropyl alcohol or ethanol, and fumaric acid, wherein if the $C_{1-4}$ alcohol is isopropyl alcohol the isopropyl alcohol is in an amount of about 1-10 volumes per total weight of O-desmethylvenlafaxine and if the $C_{1-4}$ alcohol is ethanol the ethanol is in an amount of about 1-5 volumes per total weight of O-desmethylvenlafaxine; and precipitating crystalline O-desmethylvenlafaxine fumarate Form I out of the mixture. Preferably, when the $C_{1-4}$ alcohol is isopropyl alcohol the isopropyl alcohol is in an amount of about 4-6 volumes, more preferably about 5 volumes, per total weight of O-desmethylvenlafaxine. Preferably, when the $C_{1-4}$ alcohol is ethanol the ethanol is in an amount of about 2-4 volumes, more preferably about 3 volumes, per total weight of O-desmethylvenlafaxine.

The O-desmethylvenlafaxine starting material can be either in its base form, or as a fumarate salt.

Optionally, water is also introduced into the reaction mixture.

In one specific embodiment, fumaric acid and O-desmethylvenlafaxine in the $C_{1-4}$ alcohol solvent are heated to form a reaction mixture. Heating may be carried out from about room temperature to about the reflux temperature of the solvent, preferably at about reflux temperature of the solvent. O-desmethylvenlafaxine fumarate crystalline Form I forms in the reaction mixture. The reaction mixture may then be cooled to facilitate precipitation. Cooling is generally carried out to a temperature of about 50° C. or less, preferably to about 15° C. to about 30° C., more preferably to about room temperature, to facilitate precipitation. The reaction mixture may be stirred before, during or after precipitation.

The resulting precipitate from any of the above embodiments may be recovered by conventional techniques, such as filtration. The precipitate may be dried under ambient conditions or reduced pressure, or elevated temperature. Preferably, the precipitate is dried at about 40° C. to about 60° C., more preferably at about 50° C., at a pressure of less than about 100 mmHg.

In yet another embodiment, the present invention provides another process for preparing crystalline O-desmethylvenlafaxine fumarate Form I comprising: providing a mixture of O-desmethylvenlafaxine, an aqueous solvent mixture and fumaric acid; and precipitating crystalline O-desmethylvenlafaxine fumarate Form I out of the mixture.

Preferred solvents, used to form the aqueous solvent mixture, are dimethylacetamide, $C_{3-4}$ esters, preferably ethyl acetate, and $C_{2-4}$ nitriles, preferably acetonitrile.

The solvent/water ratio in these aqueous solvent mixtures can be from about 1:2 to about 5:1, preferably from about 1:1.5 to 3.5:1. Preferably when the solvent mixture is a water/dimethylamine mixture the ratio is about 3.5:2. Preferably, when the solvent mixture is a water/ethylacetate mixture the ratio is about 1:3. Preferably when the solvent mixture is water/acetonitrile the ratio is about 1:3.5.

The mixture is preferably maintained at room temperature for an overnight period, preferably about 8 hours to about 20 hours, more preferably about 18 hours.

The resulting precipitate may be recovered by conventional techniques, such as filtration. The precipitate may be dried under ambient conditions or reduced pressure, or elevated temperature. Preferably, the precipitate is dried at about 40° C. to about 60° C., more preferably at about 50° C., preferably at a pressure of less than about 100 mmHg.

In yet another embodiment, the present invention provides another process for preparing Form I comprising: slurrying a mixture of O-desmethylvenlafaxine fumarate Forms I and II in a $C_4$-$C_8$ ether at a temperature of about 15° C. to about 30°

C., preferably about room temperature. The $C_4$-$C_8$ ether is preferably Cyclopentyl methyl ether.

The slurry is preferably maintained for an overnight period, preferably about 8 hours to about 20 hours, more preferably about 18 hours, to obtain O-desmethylvenlafaxine fumarate crystal Form I.

The resulting precipitate may be recovered by conventional techniques, such as filtration. The precipitate may be dried under ambient conditions or reduced pressure, or elevated temperature. Preferably, the precipitate is dried at about 40° C. to about 60° C., more preferably at about 50° C., preferably at a pressure of less than about 100 mmHg.

A process for preparing crystalline O-desmethylvenlafaxine fumarate Form II may comprise: providing a mixture of O-desmethylvenlafaxine, isopropyl alcohol and fumaric acid, wherein the isopropyl alcohol is in an amount of more than about 15 volumes, preferably about 15 to about 30 volumes, more preferably about 20 volumes, per total weight of O-desmethylvenlafaxine, and precipitating crystalline O-desmethylvenlafaxine Form II out of the mixture.

In yet another embodiment, the present invention provides another process for preparing crystalline O-desmethylvenlafaxine fumarate Form II comprising: providing a mixture of O-desmethylvenlafaxine, ethyl lactate, and fumaric acid, and precipitating crystal Form II of O-desmethylvenlafaxine out of the mixture.

In one specific embodiment, O-desmethylvenlafaxine, fumaric acid and the isopropyl alcohol or ethyl lactate solvent are combined to form a solution. Where the solvent is isopropyl alcohol, O-desmethylvenlafaxine and fumaric acid in the solvent may be heated to obtain a solution. Heating may be carried out from about room temperature to about reflux temperature of the solvent. The solution may than be cooled to a temperature of about 50° C. or less, preferably to about 15° C. to about 30° C., preferably to about room temperature. The solution is maintained for an overnight period, preferably about 8 hours to about 20 hours, more preferably for about 18 hours, at a temperature of about 15° C. to about 30° C., preferably room temperature, to obtain O-desmethylvenlafaxine fumarate crystal Form II. The reaction mixture may be stirred before, during or after precipitation.

The resulting precipitate from any of the above embodiments may be recovered by conventional techniques, such as filtration. The precipitate may be dried under ambient conditions or reduced pressure, or elevated temperature. Preferably, the precipitate is dried at about 40° C. to about 60° C., preferably at about 50° C., preferably at a pressure of less than about 100 mmHg.

A mixture of O-desmethylvenlafaxine fumarate crystal Forms I and II may be precipitated from a reaction mixture of O-desmethylvenlafaxine, a solvent selected from ethanol, acetone or a mixture thereof and fumaric acid, wherein when ethanol is used, the ethanol is in an amount of more than about 7 volumes per total weight of O-desmethylvenlafaxine.

Figure 3:
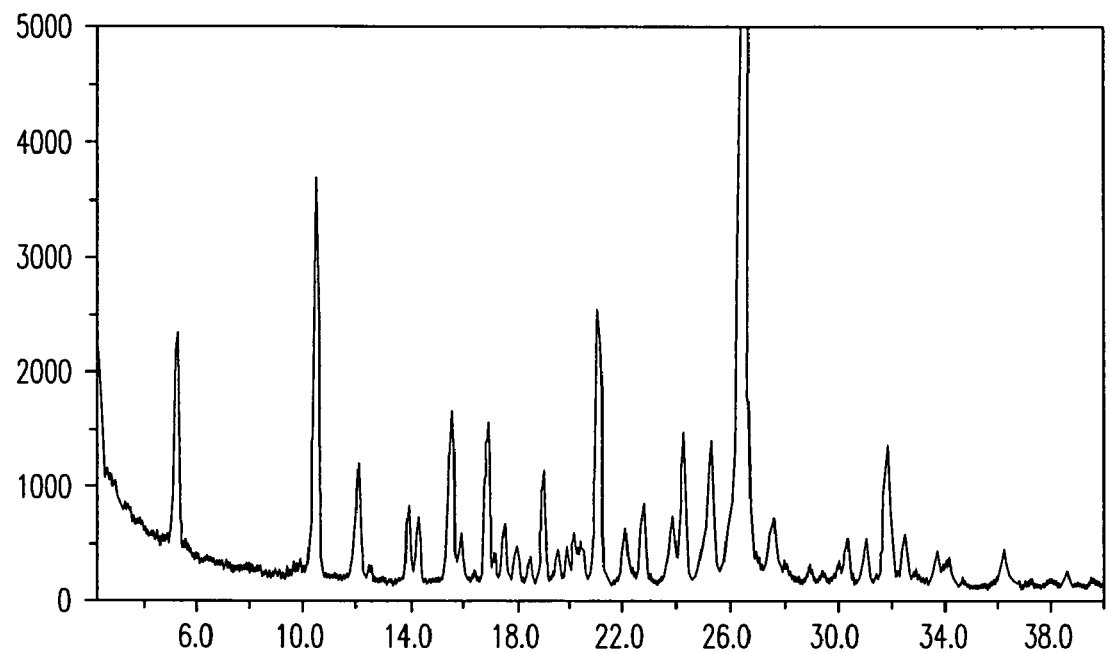
FIG. 3 illustrates a PXRD for a mixture of crystalline Forms I and II of O-desmethylvenlafaxine fumarate.

The mixture of O-desmethylvenlafaxine fumarate crystal Forms I and II can be characterized by a powder XRD pattern as depicted in FIG. 3.

In yet another embodiment, the present invention provides solid containing pharmaceutical compositions comprising one or more of the above-described crystal forms of O-desmethylvenlafaxine fumarate and a pharmaceutically acceptable excipient.

In another embodiment, the present invention provides a method of treating a patient comprising administering to a patient in need thereof a therapeutically effective amount of the above crystalline form of O-desmethylvenlafaxine fumarate. Preferably, the patient suffers from a condition which may be treated with a norepinephrine or a serotonin re-uptake inhibitor. Such patient may be suffering from depression.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

EXAMPLES

The XRD diffraction was performed on Scintag X-ray powder diffractometer model X'TRA with a solid state detector. Copper radiation of 1.5418 Å was used. The sample holder was a round standard aluminum sample holder with rough zero background. The scanning parameters were range: 2-40 degrees two-theta; scan mode: continuous scan; step size: 0.05 deg.; and at a rate of 5 deg/min.

The $^{13}$C NMR was performed at 125 MHz using Bruker Avance II+ 500 SB probe using 4 mm rotors. Magic angle was set using KBr. Homogeneity of magnetic field checked using adamantine. Parameters for Cross polarization optimized using glycine. Spectral reference set according to glycine as external standard (176.03 ppm for low field carboxyl signal)

Example 1

A 100 ml three necked flask equipped with a mechanical stirrer was charged with O-desmethylvenlafaxine (ODV) base (1 g, 3.79 mmol) and IPA (5 ml), the suspension stirred and heated to reflux. Fumaric acid (0.44 g, 3.79 mmol) in $H_2O$ (2 ml) was added. Almost clear solution was obtained and few minutes after the product started to precipitate. The slurry was gradually cooled to room temperature and stirred at room temperature for 18 hrs. Then the solid was filtered under reduced pressure, and dried for 18 hrs at 50° C. under vacuum to get ODV fumarate pure Form I. The X-ray powder diffraction pattern is substantially as depicted in FIG. 1.

Example 2

A 100 ml three necked flask equipped with a mechanical stirrer was charged with ODV base (2 g, 7.58 mmol), Fumaric acid (0.86 g, 7.58 mmol) and IPA (40 ml). The suspension stirred and heated to reflux until a clear solution was obtained. Then, the solution was gradually cooled to room temperature, while no precipitation occurred above 60° C.

The solution was stirred at room temperature for 18 hrs and then precipitation occurred. The product was filtered under reduced pressure, and dried overnight at 50° C. under vacuum to get ODV fumarate pure Form II. The X-ray powder diffraction pattern is substantially as depicted in FIG. 2.

Example 3

A 100 ml three necked flask equipped with a mechanical stirrer was charged with ODV base (2 g, 7.58 mmol), Fumaric acid (0.86 g, 7.58 mmol) and IPA (14 ml). The suspension stirred and heated to reflux, clear solution was obtained and few minutes after the product started to precipitate. The slurry was gradually cooled to room temperature and was stirred at room temperature for 18 hrs. Then, the solid was filtered under reduced pressure, and dried overnight at 50° C. under vacuum to get ODV fumarate pure Form I.

Example 4

A 100 ml three necked flask equipped with a mechanical stirrer was charged with ODV base (2 g, 7.58 mmol) and IPA (14 ml). The suspension stirred and heated to reflux and then Fumaric acid (0.86 g, 7.58 mmol) was added. Almost clear solution was obtained and few minutes after the product started to precipitate. The slurry was gradually cooled to room temperature and was stirred at room temperature overnight. Then, the solid was filtered under reduced pressure, and dried for 18 hrs at 50° C. under vacuum to get ODV fumarate pure Form I.

Examples 5-7

General Process for Slurry at Room Temperature

To a 100 ml flask equipped with a mechanical stirrer and condenser, were added ODV base fumaric acid (1:1 equivalent) and the solvent mixture. The mixture was stirred at room temperature for 18 hrs. Then the solid was filtered under reduced pressure, washed and dried in a vacuum oven for 18 hrs at 50° C. to get ODV fumarate pure Form I.

|   | Solvent | Ratio | Vol | Time | Temp. |
|---|---|---|---|---|---|
| 5 | DMA/$H_2O$ | 2/3.5 | 5 | 18 hrs | RT |
| 6 | EtOAc/$H_2O$ | 3/1 | 8 | 18 hrs | RT |
| 7 | ACN/$H_2O$ | 3.5/1 | 3 | 18 hrs | RT |

Example 8

A 1 L three necked flask equipped with a mechanical stirrer and a thermometer, was charged with ODV base (75 g, 285 mmol) and EtOH abs (225 ml). This suspension was stirred at reflux. Fumaric acid (36.5 g, 314 mmol) in $H_2O$ (112.5 ml) were added at reflux a clear solution was obtained. The solution was cooled to room temperature and stirred at room temperature for 18 hrs.

The solid was filtered under reduced pressure, washed and dried under vacuum at 50° C. to get ODV fumarate pure Form I.

Examples 9-10

To a 100 ml flask equipped with a mechanical stirrer and condenser, were added ODV fumarate Forms I+II and the solvent. The mixture was stirred at room temperature for 18 hrs. Then the solid was filtered under reduced pressure, washed and dried in a vacuum oven 18 hrs at 50° C. to get ODV fumarate pure Form I.

|   | Solvent | Vol | Temp. | Time |
|---|---|---|---|---|
| 9 | Cyclopentyl methyl ether | 10 | RT | 18 hrs |
| 10 | Cyclopentyl methyl ether | 5 | RT | 18 hrs |

Example 11

To a 100 ml flask equipped with a mechanical stirrer and condenser, were added ODV base (1 g 3.79 mmol) fumaric acid (0.5 g 4.3 mmol) and ethyl lactate (15 ml) at room temperature. A clear solution was obtained. The mixture was stirred at room temperature for 18 hrs. The solid was filtered under reduced pressure, washed and dried in a vacuum oven overnight at 50° C. to get ODV fumarate pure Form II.

Comparative Examples

Example 12

A 100 ml one necked flask equipped with a magnetic stirrer was charged with ODV base (1 g, 3.79 mmol) and EtOH (7 ml), the suspension was stirred at room temperature. Fumaric acid (0.44 g, 3.79 mmol) was added at room temperature and a clear solution was obtained after 5 minutes.

After 1 hour a massive precipitation occurred and the slurry was stirred at room temperature for 6 hours. Then the solid was filtered under reduced pressure, and dried 18 hrs at 50° C. under vacuum to get a mixture of ODV fumarate Forms I and II. The X-ray powder diffraction pattern is substantially as depicted in FIG. 3.

Example 13

A 100 ml one necked flask equipped with a magnetic stirrer was charged with ODV base (1 g, 3.79 mmol) and acetone (7 ml), the suspension was stirred at room temperature. Fumaric acid (0.44 g, 3.79 mmol) was added at room temperature. No clear solution was obtained.

The slurry was stirred at room temperature for 6 hours. Then the solid was filtered under reduced pressure, and dried 18 hrs at 50° C. under vacuum to get a mixture of ODV fumarate Forms I and II.

Example 14

A 100 ml one necked flask equipped with a magnetic stirrer was charged with ODV base (1 g, 3.79 mmol) and mixture of acetone and ethanol (50:50) (7 ml), the suspension was stirred at room temperature. Fumaric acid (0.44 g, 3.79 mmol) was added at room temperature and a clear solution was obtained after 5 minutes.

After 15 minutes the product started to precipitate. The slurry was stirred at room temperature for 3 hours and then was filtered under reduced pressure and dried 18 hrs at 50° C. under vacuum to get a mixture of ODV fumarate Forms I and II.

The invention claimed is:

1. A pure crystalline Form I of O-desmethylvenlafaxine fumarate characterized by a powder XRD pattern having any 5 peaks selected from the group consisting of peaks at: 5.3, 10.5, 12.1, 15.5, 17.9, 21.0, 22.1, 22.7, 23.8 and 24.2 degrees two theta±0.2 degrees two theta, wherein the combination of peaks selected includes at least one of the peaks at 12.1, 17.9, 22.1 or 23.8 degrees two theta±0.2 degrees two theta;

said pure crystal form I having less than about 5% by weight of Form II of O-desmethylvenlafaxine fumarate.

2. The pure crystalline Form I of O-desmethylvenlafaxine fumarate of claim 1 characterized by a powder XRD pattern having reflections at: 5.3, 10.5, 12.1, 15.5 and 17.9 degrees two theta±0.2 degrees two theta.

3. The pure crystalline Form I of O-desmethylvenlafaxine fumarate of claim 2 further characterized by a powder XRD pattern substantially as depicted in FIG. 1.

4. The pure crystalline Form I of O-desmethylvenlafaxine fumarate of claim 1 having less than about 1% by weight of Form II of O-desmethylvenlafaxine fumarate.

5. A process for preparing the crystalline O-desmethylvenlafaxine fumarate Form I according to claim 1, said process comprising:

a) providing a mixture of O-desmethylvenlafaxine, a $C_{1-4}$ alcohol solvent, and fumaric acid, wherein when the $C_{1-4}$ alcohol is isopropyl alcohol, the isopropyl alcohol is in an amount of about 1-10 volumes per total weight of O-desmethylvenlafaxine, and when the $C_{1-4}$ alcohol is ethanol, the ethanol is in an amount of about 1-5 volumes per total weight of O-desmethyl-venlafaxine, and b) precipitating crystalline O-desmethylvenlafaxine fumarate Form I from the mixture.

6. The process of claim 5, wherein when the $C_{1-4}$ alcohol is isopropyl alcohol the isopropyl alcohol is in an amount of about 5 volumes per total weight of O-desmethylvenlafaxine.

7. The process of claim 5, wherein when the $C_{1-4}$ alcohol is ethanol the ethanol is in an amount of about 3 volumes per total weight of O-desmethylvenlafaxine.

8. The process of claim 5, wherein water is introduced into the reaction mixture of step a).

9. The process of claim 5, wherein fumaric acid and O-desmethylvenlafaxine in the solvent are heated to form a reaction mixture.

10. The process of claim 9, wherein heating is carried out to about room temperature to about the reflux temperature of the solvent.

11. The process of claim 9 further comprising cooling the reaction mixture to obtain a precipitate.

12. The process of claim 1, wherein cooling is carried out to a temperature of about 50° C. to about room temperature.

13. A process for preparing crystalline O-desmethylvenlafaxine fumarate Form I according to claim 1, said process comprising:
providing a mixture of O-desmethylvenlafaxine, an aqueous solvent mixture and fumaric acid; and
precipitating crystalline O-desmethylvenlafaxine fumarate Form I out of the mixture.

14. The process of claim 13, wherein the aqueous solvent mixture comprises water and a solvent selected from the group consisting of dimethylacetamide, $C_{3-4}$ esters, and $C_{2-4}$ nitrites.

15. The process of claim 14, wherein the $C_{3-4}$ ester is ethyl acetate, and the $C_{2-4}$ nitrile is acetonitrile.

16. The process of claim 13, wherein the solvent/water ratio in the aqueous solvent mixtures is from about 1:2 to about 5:1.

17. The process of claim 16, wherein the solvent/water ratio in the aqueous solvent mixture is from about 1:1.5 to 3.5:1.

18. The process of claim 13, wherein the mixture is maintained at room temperature for about 8 hours to about 20 hours.

19. The process of claim 18, wherein the mixture is maintained at room temperature for about 18 hours.

20. A process for preparing crystalline O-desmethylvenlafaxine fumarate Form I according to claim 1, said process comprising: slurrying a mixture of O-desmethylvenlafaxine fumarate Forms I and II, in a $C_4$-$C_8$ ether.

21. The process of claim 20, wherein the $C_4$-$C_8$ ether is Cyclopentyl methyl ether.

22. The process of claim 20, wherein the slurry is maintained for a period of about 8 hours to about 20 hours to obtain O-desmethylvenlafaxine fumarate crystal Form I.

23. The process of claim 22, wherein the slurry is maintained for about 18 hours.

24. A pure crystalline Form II of O-desmethylvenlafaxine fumarate characterized by a powder XRD pattern having any 5 peaks selected from the group consisting of: peaks at 5.3, 10.5, 11.6, 16.4, 18.4, 21.0, 23.4, 24.3, 26.4 and 31.4 degrees two theta±0.2 degrees two theta, wherein the combination of peaks selected includes at least one of the peaks at 11.6, 23.4 or 31.4 degrees two theta±0.2 degrees two theta; said pure crystalline Form II having less than about 5% by weight of Form I of O-desmethylvenlafaxine fumarate.

25. The pure crystalline Form II of O-desmethylvenlafaxine fumarate of claim 24 characterized by a powder XRD pattern having reflections at: 5.3, 10.5, 11.6, 16.4 and 18.4 degrees two theta±0.2 degrees two theta.

26. The pure crystalline Form II of O-desmethylvenlafaxine fumarate of claim 25 further characterized by a powder XRD pattern substantially as depicted in FIG. 2.

27. The pure crystalline Form II of O-desmethylvenlafaxine fumarate of claim 26 having less than about 1% by weight of Form I of O-desmethylvenlafaxine fumarate.

28. A process for preparing crystalline O-desmethylvenlafaxine fumarate Form II according to claim 24, said process comprising:
providing a mixture of O-desmethylvenlafaxine, ethyl lactate and fumaric acid, and
precipitating crystal Form II of O-desmethylvenlafaxine from the mixture.

29. The process of claim 28, wherein O-desmethylvenlafaxine, fumaric acid and the solvent are combined to form a solution, and maintaining the solution for a period of about 8 hours to about 20 hours at a temperature of about 15° C. to about 30° C. to obtain O-desmethylvenlafaxine fumarate crystal Form II.

30. The process of claim 29, wherein the period is about 18 hours and the temperature is about room temperature.

31. A solid containing pharmaceutical compositions comprising one or both of the crystal forms of O-desmethylvenlafaxine fumarate of claims 1 or 24, and a pharmaceutically acceptable excipient.

32. A method of preparing a pharmaceutical composition of crystalline O-desmethylvenlafaxine fumarate comprising:
combining one or both of the crystal forms of O-desmethylvenlafaxine fumarate of claims 1 or 24 with one or more pharmaceutically acceptable excipients to obtain a pharmaceutical composition.

33. The pure crystalline Form I of O-desmethylvenlafaxine fumarate of claim 1, further characterized by a powder XRD pattern having peaks at 5.3, 10.5, 12.1 degrees two theta±0.2 degrees two theta, and at least two peaks selected from the following list of peaks at: 15.5, 16.9, 19.0, 21.0, 24.2, 25.3, and 26.4±0.2 degrees two theta±0.2 degrees two theta.

34. The pure crystalline Form I of O-desmethylvenlafaxine fumarate of claim 1, further characterized by a solid-state $^{13}C$ NMR spectrum with signals at 114.89, 139.68 and 172.44±0.2 ppm.

35. The pure crystalline Form I of O-desmethylvenlafaxine fumarate of claim 1, further characterized by a solid-state $^{13}C$ NMR spectrum having chemical shifts differences between the signal exhibiting the lowest chemical shift and another in the chemical shift range of 110 to 200 ppm of 0, 24.79 and 57.55±0.1 ppm, wherein the signal exhibiting the lowest chemical shift in the chemical shift area of 110 to 200 ppm is at 114.89±1 ppm.

36. The pure crystalline Form I of O-desmethylvenlafaxine fumarate of claim 35, further characterized by a solid state $^{13}C$ NMR spectrum substantially as depicted in FIG. 4 or a solid state $^{13}C$ NMR spectrum substantially as depicted in FIG. 5.

37. The pure crystalline Form II of O-desmethylvenlafaxine fumarate according to claim 24, further characterized by a powder XRD pattern having peaks at 14.2, 16.4, 18.4, and at least two peaks selected from the following list of peaks at: 5.3, 10.5, 11.6, 20.8, 24.3, and 26.4 degrees two theta±0.2 degrees two theta.

38. The pure crystalline Form II of O-desmethylvenlafaxine fumarate according to claim 24, further characterized by a solid-state $^{13}$C NMR spectrum with signals at 114.59, 126.44 and 133.99±0.2 ppm.

39. The pure crystalline Form II of O-desmethylvenlafaxine fumarate according to claim 24 further characterized by a solid-state $^{13}$C NMR spectrum having chemical shifts differences between the signal exhibiting the lowest chemical shift and another in the chemical shift range of 110 to 200 ppm of 0, 11.85 and 19.4±0.1 ppm, wherein the signal exhibiting the lowest chemical shift in the chemical shift area of 110 to 200 ppm is at 114.59±1 ppm.

40. The pure crystalline Form II of O-desmethylvenlafaxine fumarate according to claim 38, further characterized by a solid state $^{13}$C NMR spectrum substantially as depicted in FIG. 6, or a solid state $^{13}$C NMR spectrum substantially as depicted in FIG. 7.

* * * * *